United States Patent [19]

Raible

[11] 4,253,967

[45] * Mar. 3, 1981

[54] BLOOD TREATING METHOD

[75] Inventor: Donald A. Raible, Orange, Calif.

[73] Assignee: Bentley Laboratories, Inc., Irvine, Calif.

[*] Notice: The portion of the term of this patent subsequent to Jun. 12, 1996, has been disclaimed.

[21] Appl. No.: 28,531

[22] Filed: Apr. 9, 1979

Related U.S. Application Data

[60] Division of Ser. No. 644,451, Dec. 29, 1975, Pat. No. 4,157,965, which is a continuation-in-part of Ser. No. 542,593, Jan. 20, 1975, abandoned.

[51] Int. Cl.³ .............................................. B01D 13/00
[52] U.S. Cl. ..................................... 210/645; 210/664
[58] Field of Search ...................... 210/23 R, 436, 306, 210/335, DIG. 23, 446, 443, 448; 422/48; 55/178

[56] References Cited

U.S. PATENT DOCUMENTS

| | | | |
|---|---|---|---|
| 1,431,411 | 10/1922 | Morel et al. | 210/306 |
| 2,927,582 | 3/1960 | Berkman et al. | 128/214 |
| 2,934,067 | 4/1960 | Calvin | 128/214 |
| 3,191,600 | 5/1962 | Everett | 128/276 |
| 3,291,568 | 12/1966 | Sautter | 422/48 |
| 3,507,395 | 4/1970 | Bentley | 210/443 |
| 3,593,854 | 7/1971 | Swank | 210/446 |
| 3,664,339 | 5/1972 | Santomieri | 210/446 |
| 3,701,433 | 10/1972 | Krakauer et al. | 210/446 |
| 3,896,733 | 7/1975 | Rosenberg | 210/446 |
| 3,993,461 | 11/1976 | Leonard et al. | 210/DIG. 23 |
| 4,038,194 | 7/1977 | Luceyk et al. | 210/DIG. 23 |
| 4,056,476 | 11/1977 | Mouwen et al. | 210/DIG. 23 |
| 4,094,792 | 6/1978 | Bentley | 210/321 B |
| 4,157,965 | 6/1979 | Raible | 210/DIG. 23 |
| 4,164,468 | 8/1979 | Raible | 210/DIG. 23 |

FOREIGN PATENT DOCUMENTS 1069834 11/1959 Fed. Rep. of Germany .

OTHER PUBLICATIONS

Proceedings of the Staff Meetings of the Mayo Clinic, Mar. 1955.

Primary Examiner—Charles N. Hart
Assistant Examiner—E. Rollins Cross
Attorney, Agent, or Firm—Lyon & Lyon

[57] ABSTRACT

A method of receiving retrieved blood from the surgical field of a patient and treating the blood so that it is in condition for direct or indirect return to the patient. The method treats a relatively large volume of blood, which when received in a housing adapted to receive such blood volumes, removes air bubbles and other foreign matter. The received blood flows smoothly both to and from a fibrous membrane interposed in the path of blood flow thereby avoiding bubbling and damage of the blood. Significantly, means within the housing are provided to inhibit clotting of the blood within the housing.

7 Claims, 7 Drawing Figures

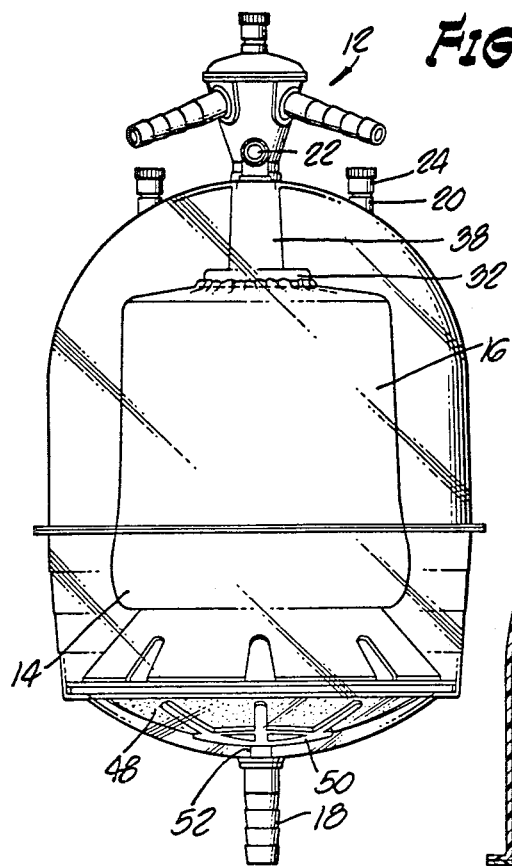
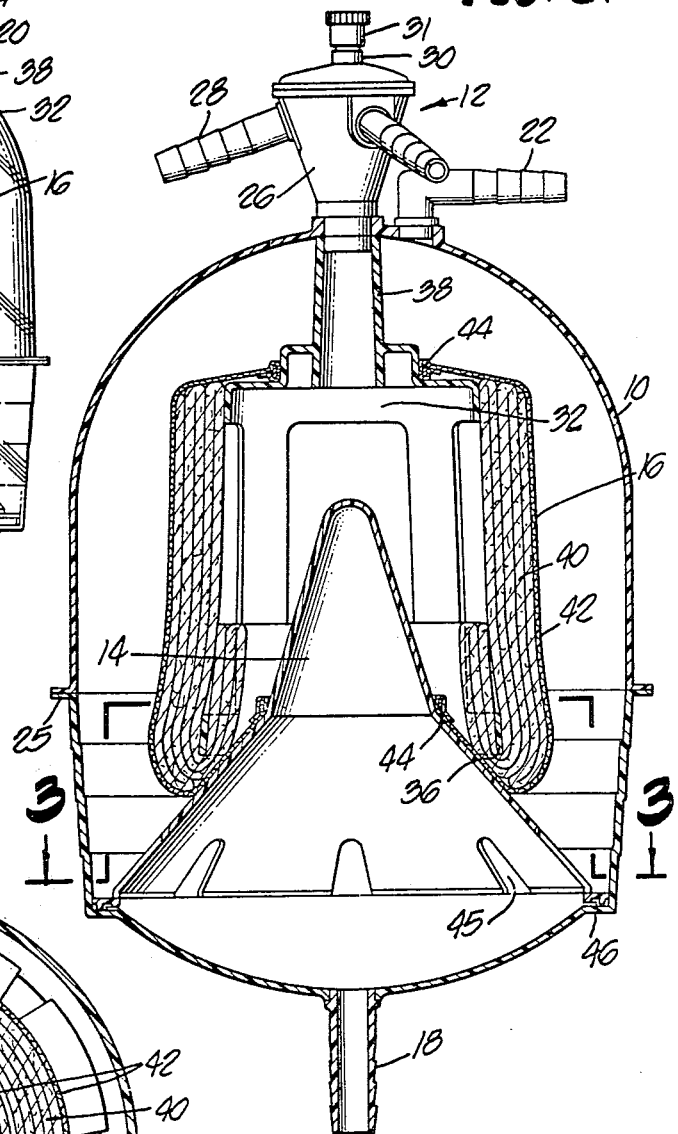
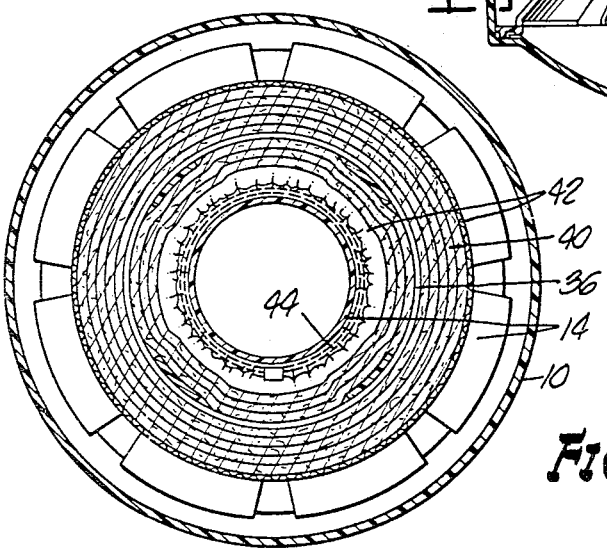

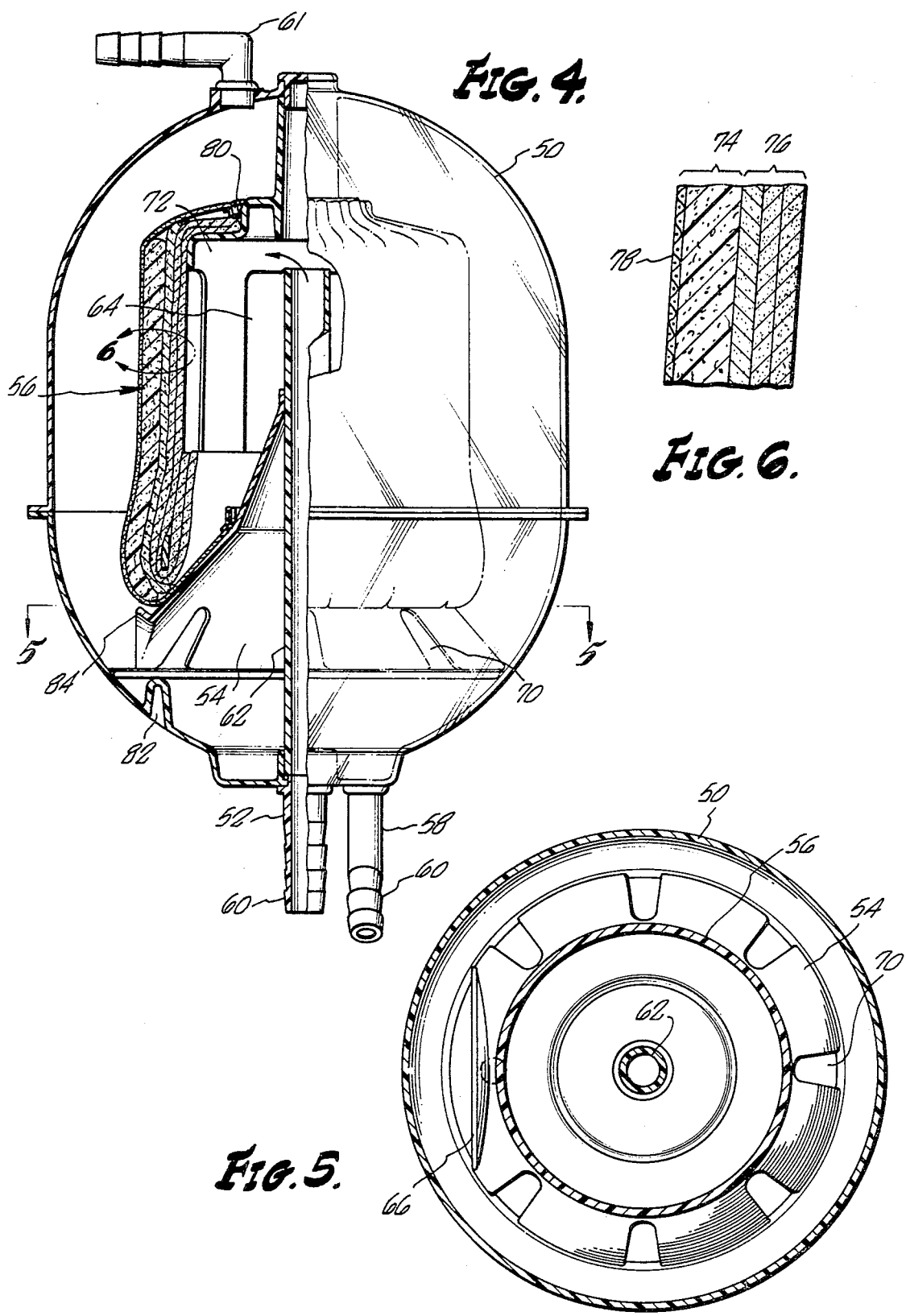

BLOOD TREATING METHOD

BACKGROUND OF THE INVENTION

This is a divisional of U.S. patent application Ser. No. 644,451 filed Dec. 29, 1975 and issued as U.S. Pat. No. 4,157,965 on June 12, 1979, which in turn is a continuation-in-part of U.S. patent application Ser. No. 542,593 filed Jan. 20, 1975 and now abandoned.

The present invention relates to a method of receiving blood retrieved from the surgical field of a patient and treating the blood so that it is in a condition for return to the patient, and, more particularly, the present invention relates to such a device having improved blood flow characteristics.

Prior art blood treating devices include generally such devices as disclosed in the U.S. Pat. Nos. of Broman, 3,087,490; Gewecke et al, 3,112,746; Collins, 3,295,297; Everett, 3,191,600; and to the present asignee Bentley Laboratories, Inc., 3,488,158, 3,507,395, 3,578,411 and 3,615,238. With respect to those prior art devices directed specifically to accomplishing the results for which the structure of this invention is intended, the U.S. Pat. No. to Bentley Laboratories, Inc., 3,507,395 offers several notable advantages. The present invention however, offers still further advantages and features.

Of particular importance in blood treating devices is the control of the blood flow through the device. Absent such control, undesired bubbling, clotting and damage to the blood can occur. Therefore, it is an important object of the present invention to provide for a disposable blood treating device of the type often referred to as a cardiotomy reservoir wherein blood retrieved from the surgical field of a patient is placed in condition for return to a patient by removing air bubbles and other foreign matter from the blood and improved control of the flow of blood through the device is maintained.

Briefly stated, the present invention includes a generally ellipsoid-shaped housing having a blood inlet means and blood outlet means with a defined blood flow path therebetween. Within the housing and interposed in the blood flow path is at least a defoamer through which the received blood flows in a radially outward direction. The defoamer is securely and concentrically mounted within the housing and maintained in a spaced relationship with respect to the interior surface thereof. Means cause the blood received to pass from the blood inlet means in a smooth relatively thin and uniform sheet radially outwardly to and through a fibrous structure of the defoaming means and from the defoamer means through a nylon bag towards the blood outlet means in a manner which avoids splashing and thus the formation of undesirable air bubbles. The spaced relationship of the defoamer with respect to the interior of the housing is maintained throughout the operation of the device and thus precludes the formation of blood clots on the downstream side of the defoamer which might otherwise form between the exterior of the defoamer and the interior of the housing. A filter within the housing may be provided for removing blood microemboli such as sticky platelets, fat agglomerates and broken red cell debris.

BRIEF DESCRIPTION OF THE DRAWINGS

A more thorough disclosure of the objects and advantages of the present invention is presented in the detailed description which follows and from the accompanying drawings in which:

FIG. 1 is a perspective side view of the blood treating device wherein a filter is incorporated;

FIG. 2 is a cross-sectional side view of a device illustrating the blood flow control means;

FIG. 3 is a cross-sectional view of the device taken along line 3—3 of FIG. 2;

FIG. 4 is a perspective side view partially in section of an alternate embodiment of the blood treating device wherein a filter is incorporated;

FIG. 5 is a cross-sectional view of the alternate embodiment taken along line 5—5 of FIG. 4;

FIG. 6 is an enlarged sectional view of the blood filter and defoamer; and

DETAILED DESCRIPTION OF THE INVENTION

Figure 7:
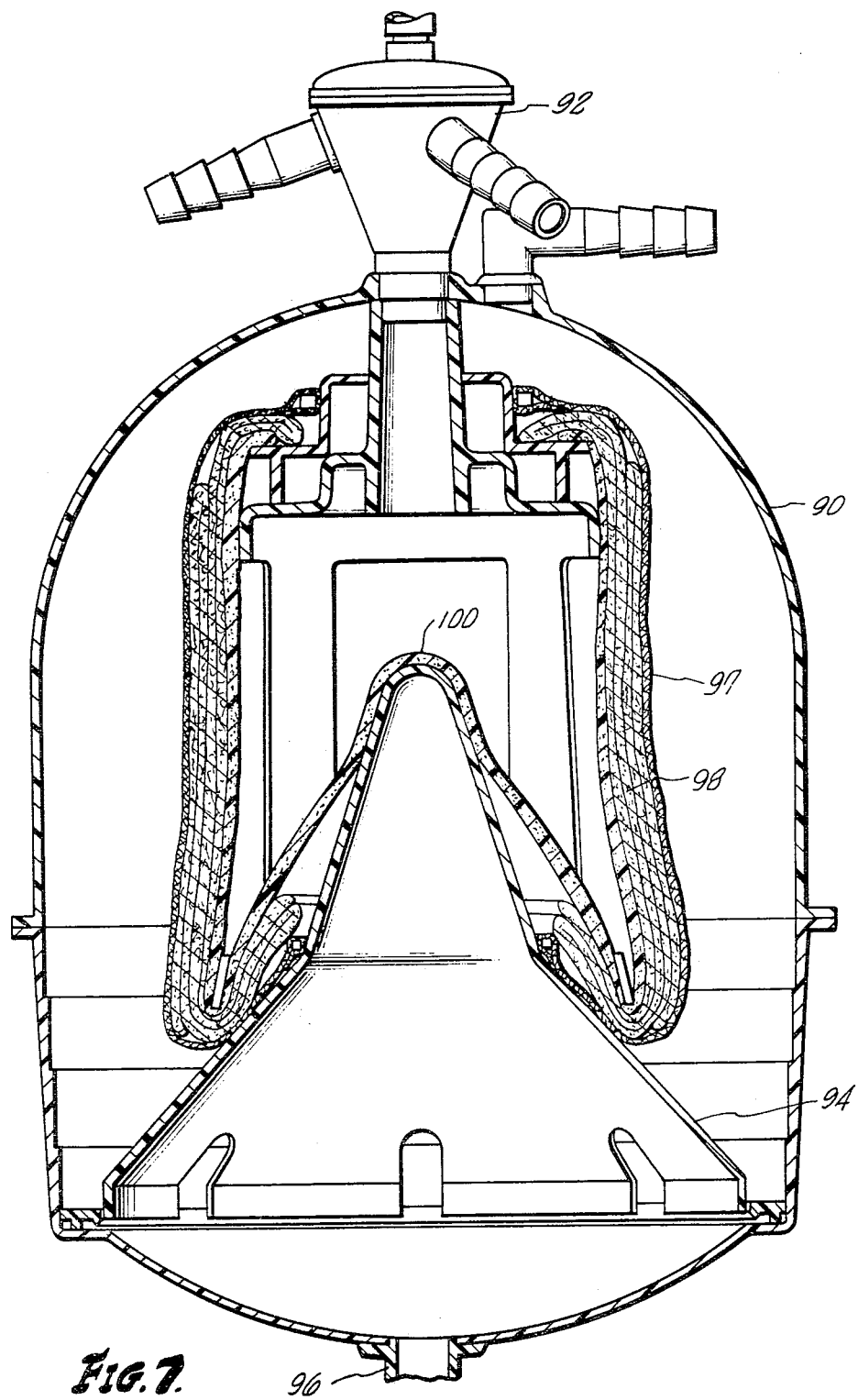
FIG. 7 is a cross-section of an alternate embodiment of the blood treating device.

The blood treating device or cardiotomy reservoir of this invention comprises generally an ellipsoidal-shaped housing 10, a blood inlet means 12, blood flow control means 14, defoaming means 16, and blood outlet means 18.

Describing now the various elements of the cardiotomy reservoir in more detail, housing 10 is provided with auxiliary inlet means 20. As shown in FIG. 1, the auxiliary inlet means or port 20 is provided with cap 24 and functions to enable the introduction of drugs or other fluids into the blood outside the defoaming means 16. The housing also includes a vent 22 for relieving pressure within the reservoir which may result from the blood being pumped into the reservoir by a positive pressure pump. The flow rate of blood through the reservoir can be accelerated by merely closing the vent. The housing is preferably made of a suitable clear, inexpensive plastic material such as that sold by the General Electric Company, under the trademark "Lexan" but it would be obvious to one skilled in the art that other suitable materials may be used. The housing is assembled by heat sealing or gluing together two generally dome-shaped sections forming sealing seam 25.

The blood inlet means 12 is comprised of a funnel member 26, a plurality of inlet nipples 28 and inlet port 30. Nipples 28 are capable of connection with flexible rubber or plastic tubing leading from the surgical field. Port 30 is provided with cap 31 and functions to enable the introduction of drugs or fluids into the blood before it passes through the defoamer means. Support member 32 includes an upwardly extending conduit or tube 38 which is in communication with the lower end of the funnel member 26 and which provides for the passage of blood into the interior of the defoamer means 16. The lower portion of the support member 32 is generally cup-shaped with rectangular apertures formed in the walls thereof. The support member functions to support filtering means 16 and to spread the interior of the primary filter means so that a greater surface area of the filter is exposed for filtering.

The defoamer means 16 is comprised of a layered polypropylene defoamer mesh 40 enclosed within a nylon filtering bag 42. Preferably, the defoamer mesh 40 and bag 42 are coated with a well-known medical silicone anti-foaming material. The filtering bag 42 is provided with tie means 44 which functions to secure the bag to the top of the support means 32 and blood flow control means 14. Blood entering through inlet means 12 must pass through defoaming means 16 before exiting the housing through outlet means 18.

The blood flow control means 14 is an integral member including an upper conically-shaped section 14a having a rounded apex and a lower base section 14b having a surface of revolution of a cone wider than that of the upper section 14a thereby providing for a more gradual flow of blood thereon. The apex of the blood flow control means 14 is spaced from and concentric with the tube 38 and blood from the tube 38 is divided by the apex into a sheet of flow on the surface of the upper section 14a.

The defoamer means 16 surrounds the upper section 14a of the blood flow control means 14 and the lower end of the filtering bag is tightly secured to the surface of the base section 14b by tie means 44. The conical shape of the blood flow control means 14 serves to maintain the defoamer means 16 and more particularly the nylon bag 42 thereof in a taut condition thereby preventing the contact of the filter means with the interior walls of the housing 10 during operation of the device. Bag 42 also serves to filter the blood.

The base section 14b at the lower end thereof is provided with a plurality of notches through which the blood flows into the blood outlet means. Because of the arrangement of the defoamer means 16 with respect to the surface of the base section 14b and the gradual slope of that surface the blood after passing through the defoamer means 16 passes towards the blood outlet means without splashing and thus the formation of air bubbles in the blood is avoided.

As shown in FIG. 1, there is positioned below control means 14 a filtering means 48. Filtering means 48 is capable of removing blood microemboli such as sticky platelets, fat agglomerates and broken red cell debris. As described in a copending application for "Device for Removing Blood Microemboli," Ser. No. 348,588, the disclosure of which is incorporated herein by reference, the filter 48 is preferably comprised of a plurality of layers each consisting of a foamed open cell polyurethane. Each layer has a different effective pore size and the filter is formed by positioning the layers in order of decreasing pore size. It is preferred that the filtering means 48 be comprised of three layers wherein the first layer has an effective pore size of approximately 150 microns, the second layer has an effective pore size of approximately 75 microns and the third layer having an effective pore size of approximately 30 microns. The filtering means 48 is positioned in the reservoir so that the layer with the largest effective pore size is contiguous to control means 14. The filtering means 48 is supported by spider 50. Spider 50 is comprised of a disc having apertures formed therein and arms extending out therefrom and a supporting base 52 which is capable of insertion into outlet means 18. As described in detail below, the microemboli filter may alternatively be disposed around the blood flow control means 14 contiguous to the defoamer means 16, thereby providing a greater effective filter area.

In operation, the blood is pumped from the surgical field of a patient through a flexible conduit by means of a roller pump. The blood is pumped into the cardiotomy reservoir device through nipples 28 of inlet means 12. The blood is then moved down through tube 38 of support member 32 and impinges upon the apex of the blood control means 14. The blood then flows down the outer surface of the blood control means until it encounters the defoamer means 16. The blood passes through the defoamer means 16 and continues to flow down the remaining base section of the blood flow control means 14. The blood then flows through notches 45 formed in the base section 14b and exits the housing through outlet means 18. In the embodiment of FIG. 1, the blood passes through a microemboli filter means 48 comprised of a plurality of polyurethane layers after passing through the defoamer and then exits the housing through outlet means 18. After exiting the housing the blood can be returned directly to the patient or passed into an oxygenator in a cardiopulmonary bypass unit.

In FIG. 7 is shown a similarly-shaped blood treating device wherein the microemboli filter is disposed around the blood flow control means to provide a greater effective filter area. The blood treating device comprises housing 90, blood inlet means 92, blood flow control means 94, blood outlet means 96 and nylon filtering bag 97 which encloses defoamer mesh 98 and microemboli filter 100. In operation, the blood enters the device through inlet 92 and contacts microemboli filter 100. The blood flows through microemboli filter 100 through defoamer mesh 98 and filtering bag 97 down the control means 94 and exits the device through outlet 96.

In FIGS. 4 and 5 is shown an alternate embodiment of a blood treating device according to the present invention comprising a similarly-shaped housing 50, a blood inlet means 52, a similarly-formed blood flow control means 54, a defoamer 56 and a blood outlet means 58.

The blood inlet and outlet means are provided with nipples 60 to enable connection with flexible rubber or plastic tubing leading to and from the surgical field. The housing is also provided with vent 61 which functions to relieve excess pressure within the reservoir. The inlet means 52 is attached to conduit 62 which extends through the blood flow control means 54 into the central portion 64 of the interior of the housing 50 defined by defoamer means 56. The similarly-shaped blood flow control means 54 is comprised of a generally conically-shaped body having a section 55 of the lower portion of the side wall cut away. The control means 54 is provided with an aperture formed in its apex for receiving conduit 62 and with notches 70 formed in the lower portion of the side wall of the control means. The device is also provided with support member 72. The lower portion of support member 72 is generally cup-shaped having rectangular apertures formed in the wall and functions to support defoamer means 56 contiguous with blood flow control means 54. The support member 72 thus requires the blood exiting the central portion 64 of the interior of the housing to flow through defoaming means 56 disposed around the support member.

Referring to FIG. 6, the defoamer means 56 is comprised of a layered defoamer mesh 74 consisting of polypropylene and a nylon filtering bag 78. In its preferred embodiment, the device is also provided with a microemboli filter 76 comprising a plurality of layers and preferably consists of open celled foamed polyurethane. The layers of the microemboli filter 76 each have differing effective pore sizes and are positioned in order of decreasing pore size where the layer having the largest effective pore size is located proximate to the primary filter 74. It is preferred that the microemboli filter be comprised of three layers having pore sizes of approximately 150, 75 and 30 microns respectively. The filtering means is also provided with a nylon bag 78 having a tie means 80 to enclose the primary and microemboli filter thereby preventing expansion thereof and to secure the filter to support means 72 and blood flow control means 54.

The blood treating device may also be provided with a lower level alarm sensor. The sensor is preferably a photoelectric sensor and is positioned in a recess 82 formed in housing 50 directly below section 66 of control means 54. The sensor is pointed upwardly past control means 54 into the interior of the housing and is capable of sensing the level of the blood in the housing. The sensor sounds an alarm if the level goes below some predetermined point thereby preventing accidental infusion of air into a patient. The control means is further provided with lip 84 to prevent blood from splashing on recess 82 and causing false alarms.

In operation, the blood enters the device through inlet 52 and moves upwardly through conduit 62. The blood exits conduit 62 into the central portion 64 of the interior of housing 50 and flows down the exterior of conduit 62 and onto blood flow control means 54. The blood flows down the blood flow control means 54 through defoamer means 56. The blood then flows through notches 70 formed in the flow control means 54 and exits the housing through outlet means 58.

From the foregoing it is apparent that the present invention provides for a blood treating device or more particularly a cardiotomy reservoir having improved blood flow characteristics. In particular, the device of the present invention provides for the control of blood flow both into and from a defoamer means whereby received blood is smoothly divided and uniformly distributed to the defoamer means in the form of sheet of flow and then passes from the filter means toward a blood outlet without splashing.

The present invention also precludes clotting of the blood as a result of blood being trapped between the exterior of the defoamer means and the interior walls of the housing. This is precluded as a result of the structural support provided for the defoamer means which maintains the defoamer means in a fixed relationship with respect to the housing.

Having fully described my invention, it is to be understood that I do not wish to be limited to the details herein set forth, but my invention is of the full scope of the appended claims.

I claim:

1. A method for receiving and treating blood during surgical procedures comprising:
   receiving blood into a housing through a blood inlet at the top of said housing and passing said blood through a predetermined blood flow path through said housing and outwardly through a blood outlet positioned at the bottom of said housing;
   removing air bubbles and other foreign material from said blood interposed in said blood flow path by defoamer means through which said blood flows radially outward, said defoamer means including a layer of defoamer material extending about a defined interior section of said housing into which blood flows from said blood inlet means, said defoamer means being positioned such that blood flow from the interior of said housing to the blood outlet means must pass through said defoamer means; and
   controlling said blood flow by passing said blood uniformly and substantially radially outwardly along a substantially conical surface toward said defoamer means thereby preventing splashing of the blood, said substantially conical surface being further defined as being positioned within said interior section defined by said layer of defoamer material and about which said layer of defoamer material extends said apex of said conical surface being positioned below and spaced apart from said blood inlet means.

2. The method claimed in claim 1 wherein said method is further defined as including:
   securing said defoamer means to a support thereby maintaining a fixed relationship between said defoamer means and said interior of said housing.

3. The method claims in claim 1 further including:
   filtering said blood prior to said blood flow passing outwardly from said blood outlet.

4. A method for receiving and treating blood during surgical procedures comprising:
   receiving blood into a housing through a blood inlet at the top of said housing and passing said blood through a predetermined blood flow path through said housing and outwardly through a blood outlet positioned at the bottom of said housing;
   removing air bubbles and other foreign material from said blood interposed in said blood flow path by defoamer means through which said blood flows radially outward, said defoamer means including a layer of defoamer material extending about a defined interior section of said housing into which blood flows from said blood inlet means, said defoamer means being positioned such that blood flow from the interior of said housing to the blood outlet means must pass through said defoamer means;
   controlling said blood flow by passing said blood uniformly and substantially and radially outwardly along a substantially conical surface toward said defoamer means thereby preventing splashing of the blood, said substantially conical surface being further defined as being positioned within said interior section defined by said layer of defoamer material and about which said layer of defoamer material extends said apex of said conical surface being positioned below and spaced apart from said blood inlet means;
   securing said defoamer means to support thereby maintaining a fixed relationship between said defoamer means and said interior of said housing;
   filtering said blood flow prior to said blood flow passing outwardly from said blood outlet.

5. A method for receiving and treating blood during surgical procedures comprising:
   receiving blood into a housing through a blood inlet at the top of said housing and passing said blood through a predetermined blood flow path through said housing and outwardly through a blood outlet positioned at the bottom of said housing;
   removing air bubbles and other foreign material from said blood interposed in said blood flow path by defoamer means through which said blood flows radially outward, said defoamer means including a layer of defoamer material extending about a defined interior section of said housing into which blood flows from said blood inlet means said defoamer means being positioned such that blood flow from the interior of said housing to the blood outlet means must pass through said defoamer means; and passing said blood uniformly and substantially radially outwardly, by passing said blood onto a conical surface of porous material through which at least a portion of said blood received for treatment is passed, said substantially conical surface being further defined as being positioned within said interior section defined by said layer of defoamer material and about which said layer of defoamer material extends, said apex of said conical surface being positioned below and spaced apart from said blood inlet means, said blood being passed by said conical surface, toward said defoamer means thereby preventing splashing of the blood.

6. The method claimed in claim 5 wherein said method is further defined as including:
securing said defoamer means to a support thereby maintaining a fixed relationship between said defoamer means and said interior of said housing.

7. The method claimed in claim 5 further including:
filtering said blood prior to said blood flow passing outwardly from said blood outlet; and
wherein said porous material is further defined as a microemboli filter material.

* * * * *